United States Patent [19]

Sugisaki et al.

[11] Patent Number: 4,465,670

[45] Date of Patent: Aug. 14, 1984

[54] METHOD FOR THE TREATMENT OF SYSTEMIC LUPUS ERYTHEMATOSUS AND PRIMARY GLOMERULONEPHRITIS AND AGENT THEREFOR

[75] Inventors: Tetsuzo Sugisaki, Urawa; Shinichi Morisue, Tokyo, both of Japan

[73] Assignee: Dainippon Pharmaceutical Co., Ltd., Osaka, Japan

[21] Appl. No.: 401,144

[22] Filed: Jul. 23, 1982

[51] Int. Cl.³ ................ A61K 37/02; A61K 35/14
[52] U.S. Cl. ............................ 424/177; 424/101; 260/112 R; 260/112 B
[58] Field of Search .............. 260/112.5 R, 112 R; 424/177, 101

[56] References Cited

U.S. PATENT DOCUMENTS

| | | | |
|---|---|---|---|
| 2,543,215 | 2/1951 | Williams | 424/177 |
| 3,763,135 | 11/1973 | Shanbrom | 424/177 |
| 4,059,571 | 11/1977 | Tomibe et al. | 260/112 B |
| 4,093,606 | 6/1978 | Coval | 424/177 |
| 4,124,576 | 11/1978 | Coval | 424/177 |
| 4,165,370 | 8/1979 | Coval | 260/112 B |
| 4,256,631 | 3/1981 | Yokoo et al. | 424/101 |
| 4,296,027 | 11/1981 | Condie | 424/101 |
| 4,322,403 | 3/1982 | Bünning | 424/101 |
| 4,329,331 | 5/1982 | Kallick | 424/88 |

OTHER PUBLICATIONS

Hitzig et al., *Birth Defects*, 1975, pp. 339–342.
Sano et al., *The Journal of Immunology*, vol. 126, No. 2, Feb. 1981, pp. 538–539.
Anderson et al., *J. Clin. Invest.*, vol. 66, Aug. 1980, pp. 353–360.
Skvaril et al., *Int. Archs Allergy Appl. Immun.*, 57, 375–378 (1978).
Masuho et al., *Vox Sang*, 32, 290–295 (1977).
Budman, *Arthritis and Rheumatism*, 20, No. 3, 829–833 (1977).
Skvaril, *Int. Archs Allergy Appl. Immun.* 57, 375–378 (1978).
Sgauris, *Vox Sang*, 13, 71–85 (1967).
Masuho, *Vox Sang*, 32, 175–181 (1977).
Polson, *Vox Sang*, 23, 107–118 (1972).
Stephan, *Vox Sang*, 20; 422–457 (1971).
Stephan, *Vox Sang*, 28, 422–437 (1975).

*Primary Examiner*—Delbert R. Phillips
*Assistant Examiner*—F. T. Moezie
*Attorney, Agent, or Firm*—Wegner & Bretschneider

[57] ABSTRACT

A method for the treatment of diseases such as systemic lupus erythematosus and primary glomerulonephritis by administering a γ-globulin having Fc fragment to patients suffering from such diseases in parenteral route (particularly intravenously) and a preparation useful for the treatment. The γ-globulin having Fc fragment is usually used in the form of a preparation thereof in admixture with a conventional liquid carrier on diluent for injection, including a plasmin-treated human γ-globulin preparation, a sulfonated human γ-globulin preparation and a polyethylene glycol-treated human γ-globulin preparation.

7 Claims, No Drawings

METHOD FOR THE TREATMENT OF SYSTEMIC LUPUS ERYTHEMATOSUS AND PRIMARY GLOMERULONEPHRITIS AND AGENT THEREFOR

The present invention relates to a method for the treatment of diseases such as systemic lupus erythematosus and primary glomerulonephritis by administering a γ-globulin having Fc fragment to patients suffering from such diseases by parenteral route, particularly by intravenous route, and also an agent useful for the treatment.

It is well known that γ-globulin preparations are useful as an agent in supplementary therapy of primary immune disorder and in passive immunotherapy for the prevention of viral infections and for the treatment of severe infections wherein they are used together with antibiotics, and such preparations are commercially available.

Such diseases as systemic lupus erythematosus and primary glomerulonephritis are usually treated by using cortico-steroids or cytotoxic agents. However, these drugs are not effective for fundamental therapy of such diseases and occasionally give serious side effects when they are continuously used for a long period of time. Thus, it has been desired to develop a fundamental therapeutic method effective for such diseases.

The present inventors have newly found that γ-globulin having Fc fragment is extremely useful for the treatment of these systemic lupus erythematosus and primary glomerulonephritis. It is known that these diseases are induced by deposits of immune complexes, i.e. certain antigen-antibody complexes (e.g. DNA-antiDNA antibody IgG), and it has now been found that such deposits of antigen-antibody complexes can be dissolved or made to disappear by administering a γ-globulin having Fc fragment by parenteral route, particularly by intravenous route, and hence, it is very useful for the fundamental therapy of these diseases.

It has been considered that in case of glomerulonephritis, the antigen-antibody complexes deposit on various places in a blood vessel, particularly in renal glomerular capillary walls, whereby the complement system is activated to result in release of amines activating blood vessel permeability. Besides, the present inventors have found that the antigen-antibody complexes themselves become an antigen and react with its antibody (rheumatoid factor) and deposit largely by chain reaction, which causes glomerulonephritis. Systemic lupus erythematosus will also be induced.

It is assumed that when γ-globulin having Fc fragment is applied to the diseased parts deposited with the complexes, the Fc fragment of γ-globulin binds excessively thereto and thereby the antigen-antibody complexes in the deposits are cleaved and decomposed to result in dissolution (dissociation) of the deposits.

An object of the present invention is to provide a method for the fundamental treatment of systemic lupus erythematosus and primary glomerulonephritis. Another object of the invention is to provide an agent useful for the method as set forth above, which comprises a γ-globulin having Fc fragment as an effective ingredient. A further object of the invention is to provide a method for the treatment of the diseases by administering the agent as set forth above to patients suffering from such diseases by parenteral route, particularly by intravenous route. These and other objectives and advantages of the invention will be apparent to persons skilled in the art from the following description.

According to the present invention, such diseases as systemic lupus erythematosus and primary glomerulonephritis including membranous nephropathy and membranoproliferative glomerulonephritis can fundamentally be remedied by administering parenterally (e.g. intravenously) an agent comprising as an effective ingredient a γ-globulin having Fc fragment to the patients suffering from the diseases.

The γ-globulin having Fc fragment includes all γ-globulins having Fc fragment which can be obtained by subjecting a native human γ-globulin to any chemical treatment and enzymatic treatment and can be administered by intravenous route. Suitable examples of such γ-globulins are a plasmin-treated human γ-globulin (cf. Int. Archs Allergy Appl. Immun, 57, 375-378 (1980); and Vox Sang., 13, 71-85, 1967); a sulfonated human γ-globulin (cf. U.S. Pat. Nos. 4,059,571, Vox Sang., 32, 175-181, 1977, and Vox Sang., 32, 290-295, 1977); a polyethylene glycoltreated human γ-globulin (cf. U.S. Pat. Nos. 4,124,576 and 3,763,135, and Vox Sang., 23, 107-118, 1972); a β-propiolactone-treated human γ-globulin (cf. Z. Klin. Chem., 7, 282, 1969, Vox Sang., 28, 422-437, 1975, and Vox Sang., 20, 442-457, 1971); an alkylated (dithiothreitol/iodoacetamide) human γ-globulin (cf. Arzneim.-Forsch./Drug Res., 30(II), Nr. 9, 1484-1486); and an acid-treated (pH4) human γ-globulin (cf. Vox Sang., 13, 93-103, 1967). Among these, the plasmin-treated human γ-globulin, sulfonated human γ-globulin and polyethylene glycol-treated human γ-globulin are particularly useful.

These γ-globulins having Fc fragment are usually used in the form of a preparation suitable for injection, particularly for intravenous injection. Such a preparation can be prepared by dissolving a γ-globulin having Fc fragment in a conventional liquid carrier or diluent suitable for injection, such as purified water, a physiological saline solution. The preparation may optionally contain other conventional additives, such as isotonic agents (e.g. glucose, saline, etc.), stabilizers (e.g. glycine, thimerosal, etc.), preservatives, pH adjusting agents, or the like. The preparation contains the active γ-globulin having Fc fragment in an amount of 500 to 10,000 mg per dose unit. The preparations useful in the present invention include also some commercially available preparations of human γ-globulin having Fc fragment.

The preparation of the present invention is usually administered by intravenous injection. The dose of the active γ-globulin may vary with age of patients, kinds and severity of the diseases to be treated, or the like, but is usually in the range of 10 to 500 mg/kg/day, preferably 20 to 100 mg/kg/day (as γ-globulin). In adults, the dose is usually in the range of 500 to 25,000 mg/day, preferably 1,000 to 5,000 mg/day (as γ-globulin). The preparation containing γ-globulin having Fc fragment is usually injected by intravenous route once a day for one to several weeks in a continuous way, but the dose may be divided and administered two to four times per day and the administration period may be shortened or elongated in accordance with the degree of symptom of the patients. Besides, other drugs such as cytotoxic agents (e.g. cyclophosphamide, 6-mercaptopurine) and steroidal preparations (e.g. predonisolone, betamethasone) may optionally be used together with the present γ-globulin preparations.

The effectiveness of the present preparation on the diseases is proved by immunological theory based on the analysis of cause of diseases and also by the clinical tests as mentioned hereinafter.

The preparation of the present invention was tested as to the effect on dissolution of deposits of antigen-antibody complexes.

Experiment

A piece of renal tissue was obtained from three patients with membranous nephrophathy, two patients with membranoproliferative glomerulonephritis and three patients with systemic lupus erythematosus by renal biopsy, and frozen sections (thickness:4 μm) were prepared from the renal tissues. The test samples from 8 patients were subjected to the following test.

The γ-globulin preparations used in the test were a plasmin-treated human γ-globulin preparation for injection, a sulfonated human γ-globulin preparation for injection, a polyethylene glycol-treated human γ-globulin for injection, and a pepsin-treated human γ-globulin for injection (cf. Dtsch. med. Wschr., 87, 1643–1650, 1962).

Each γ-globulin preparation was dissolved in distilled water to prepare test solutions containing the γ-globulin in a concentration of 5%, 1% and 0.1%. The test solutions were each added to the test samples. After reacting for one hour, the test samples thus treated were washed with a phosphate buffered saline (pH 7.2, 0.15 M) for 30 minutes. The above procedure was repeated four times. As a reference, the same procedure as above was carried out except that the phosphate buffered saline was used instead of the test solution.

The test samples thus treated were investigated by immunofluorescence analysis. As a result, in the reference samples, widely spreaded deposits of antigen-antibody (IgG) complexes were observed in renal glomerular capillary walls. On the other hand, in case of the test samples treated with the preparations of a γ-globulin having Fc fragment, i.e. plasmin-treated γ-globulin preparation, sulfonated γ-globulin preparation, and polyethylene glycol-treated γ-globulin preparation, no or little deposit of antigen-antibody (IgG) complexes was observed in 5% to 0.1% concentrations. However, in the test samples treated with the pepsin-treated γ-globulin preparation wherein the Fc fragment is not contained, wide deposits of antigen-antibody, (IgG) complexes were observed even in 5% concentration like in the reference samples.

Some clinical test results of the present preparation are illustrated below.

Clinical Test 1

The patient was a man (45 years old) having proteinuria and edema as the chief complaint who was diagnosed as having membranous nephropathy by renal biopsy. There were remarkably observed coarse glanular deposits of human antibody (IgG) complexes and complement C$_3$ along the renal glomerular capillary walls.

A plasmin-treated γ-globulin preparation for injection was intravenously administered to the patient in a dose of 2,500 mg. (as γ-globulin) once a day for three weeks. After one week from the initiation of the treatment, the proteinuria and edema were remarkably improved. After three weeks, the patient was examined by renal biopsy. As a result, the deposits of human antibody (IgG) complexes and complement C$_3$ were clearly decreased, by which the effectiveness of the preparation was proved.

Clinical Test 2

The patient was a woman (38 years old) having proteinuria and edema as the chief complaint who was diagnosed as having membranous nephropathy by renal biopsy.

A plasmin-treated γ-globulin preparation for injection was intravenously administered to the patient in a dose of 5,000 mg (as γ-globulin) discontinuously, i.e. three times in a week for two weeks. As a result, the proteinuria was remarkably decreased and the systemic edema (with feeling of stiff hand) was also remarkably improved.

Clinical Test 3

The patient was a man (38 years old) having proteinuria and edema as the chief complaint who was diagnosed as having membranoproliferative glomerulonephritis by renal biopsy.

A plasmin-treated γ-globulin preparation for injection was intravenously administered to the patient in a dose of 5,000 mg (as γ-globulin) three times in a week (totally 8 times). As a result, the proteinuria was remarkably decreased, and the systemic syndrome was also extremely improved.

Clinical Test 4

The patient was a woman (30 years old) with typical state of systemic lupus erythematosus, such as erythema of the face, proteinuria and epilation. There were observed granular deposits of human antibody (IgG) complexes along dermal-epidermal junction and glomerular capillary walls by skin and renal biopsy.

A plasmin-treated human γ-globulin preparation for injection was intravenously administered to the patient in a dose of 2,500 mg (as γ-globulin) once a day for three weeks in continuous way, wherein a steroidal agent (predonisolone) was co-administered. By this treatment, the clinical state of skin was improved and the proteinuria disappeared. Besides, the deposits of the antibody (IgG) complexes were almost completely dissolved in both of skin and renal glomerulus, which was confirmed by biopsy. There was no sign of relapse thereafter.

Clinical Test 5

The patient was a woman (29 years old) with state of systemic lupus erythematosus and having the same symptoms as the patient in the above Clinical Test 4.

A plasmin-treated human γ-globulin preparation for injection was intravenously administered to the patient in a dose of 5,000 mg (as γ-globulin) on alternate days (totally four times). By this treatment, the clinical state of skin was improved, and the proteinuria was also remarkably decreased.

What is claimed is:

1. A method for the treatment of the diseases lupus erythematosus and primary glomerulonephritis, which consisting essentially of administering an amount of a γ-globulin having Fc fragment to a patient by parenteral route effective to dissolve the immune complexes inducing those diseases.

2. A method according to claim 1, wherein the γ-globulin having Fc fragment is administered by intravenous injection in a dose of 10 to 500 mg/kg/day.

3. A method according to claim 1, wherein the γ-globulin having Fc fragment is used in the form of a preparation of 500 to 10,000 mg of a γ-globulin having Fc fragment in admixture of a conventional liquid carrier or diluent for injection.

4. A method according to claim 3, wherein the preparation is a plasmin-treated human γ-globulin preparation.

5. A method according to claim 3, wherein the preparation is a sulfonated human γ-globulin preparation.

6. A method according to claim 3, wherein the preparation is a polyethylene glycol-treated human γ-globulin preparation.

7. A method according to claim 1, wherein the γ-globulin, having Fc fragment, is a member selected from the group consisting of a plasmin-treated human γ-globulin, a polyethylene glycol-treated human γ-globulin, and a sulfonated human γ-globulin.

* * * * *